United States Patent
Gomori et al.

(10) Patent No.: US 10,814,018 B2
(45) Date of Patent: Oct. 27, 2020

(54) ISOTOPICALLY LABELED DEOXY-GLUCOSE AND DERIVATIVES THEREOF, COMPOSITIONS COMPRISING THEM AND USES THEREOF

(75) Inventors: Moshe Gomori, Jerusalem (IL); Hyla Allouche-Arnon, Rehovot (IL); Rachel Katz-Brull, Modi'in-Maccabim-Re'ut (IL)

(73) Assignee: HADASIT MEDICAL RESEARCH SERVICE & DEVELOPMENT LTD., Jerusalem (IL)

( * ) Notice: Subject to any disclaimer, the term of this patent is extended or adjusted under 35 U.S.C. 154(b) by 384 days.

(21) Appl. No.: 13/881,585

(22) PCT Filed: Oct. 25, 2011

(86) PCT No.: PCT/IL2011/000823
§ 371 (c)(1),
(2), (4) Date: Apr. 25, 2013

(87) PCT Pub. No.: WO2012/056447
PCT Pub. Date: May 3, 2012

(65) Prior Publication Data
US 2013/0230468 A1 Sep. 5, 2013

Related U.S. Application Data

(60) Provisional application No. 61/406,356, filed on Oct. 25, 2010.

(51) Int. Cl.
*A61K 49/10* (2006.01)
*C07B 59/00* (2006.01)
*C07H 3/08* (2006.01)

(52) U.S. Cl.
CPC ............ *A61K 49/10* (2013.01); *C07B 59/005* (2013.01); *C07H 3/08* (2013.01)

(58) Field of Classification Search
None
See application file for complete search history.

(56) References Cited

U.S. PATENT DOCUMENTS

| | | | |
|---|---|---|---|
| 5,439,803 A * | 8/1995 | Ross | C12Q 1/54 435/105 |
| 6,466,814 B1 | 10/2002 | Ardenkjaer-Larsen et al. | |
| 6,574,495 B1 | 6/2003 | Golman et al. | |
| 6,574,496 B1 | 6/2003 | Golman et al. | |
| 7,256,047 B2 | 8/2007 | Malloy et al. | |

FOREIGN PATENT DOCUMENTS

| | | | |
|---|---|---|---|
| WO | 0073325 A1 | 12/2000 | |
| WO | 03023432 A1 | 3/2003 | |
| WO | 03068919 A2 | 8/2003 | |
| WO | 2004016156 A2 | 2/2004 | |
| WO | 2004042360 A2 | 5/2004 | |
| WO | 2005086612 A2 | 9/2005 | |
| WO | 2006050130 A2 | 5/2006 | |
| WO | 2007025238 A2 | 3/2007 | |
| WO | 2007044867 A2 | 4/2007 | |
| WO | 2007052274 A2 | 5/2007 | |
| WO | WO 2008086534 A1 * | 7/2008 | ............ A61K 49/10 |
| WO | 2010000409 A2 | 1/2010 | |

OTHER PUBLICATIONS

Yoshimoto et al. Characterization of acetate metabolism in tumor cells in relation to cell proliferation: acetate metabolism in tumor cells. 2001 Nucl. Med. Biol. 28: 117-122.*

Yun et al. 18F-FDG PET in characterizing adrenal lesions detected on CT or MRI. 2001 J. Nucl. Med. 42: 1795-1799.*

Kanazawa et al "19F NMR of 2-Deoxy-2-fluoro-D-glucose for Tumor Diagnosis in Mice. An NDP-Bound Hexose Analog as a New NMR Target for Imaging" NMR Biomed. 10, 35-41 (1997).

Yorimitsu et al "Synthesis and Bioimaging of Positron-Emitting 15O-Labeled 2-Deoxy-D-glucose of Two-Minute Half-Life", Chem. Asian J. 2, 57-65 (2007).

Uldry et al "GLUT2 is a high affinity glucosamine transporter" FEBS Letters, 524, 199-203 (2002).

Reineri et al "Para-hydrogenated glucose derivatives as potential 13C-hyperpolarized probes for magnetic resonance imaging", J Am Chem Soc, 132 , 7186-7193 (2010).

Bluck et al "13C- and 2H-labelled glucose compared for minimal model estimates of glucose metabolism in man" Clin. Sci. 109, 513-521 (2005).

Vijayaraghavan et al "Acute toxicity and cardio-respiratory effects of 2-Deoxy-D-Glucose: A promising radio sensitiser" Biomed. Environ. Sci. 19, 96-103 (2006).

Harada et al "Selection of endogenous 13C substrates for observation of intracellular metabolism using the dynamic nuclear polarization technique" Jpn. J. Radiol. 28(2), 173-9 (2010).

Adams R.W. et al "Reversible Interactions with para-Hydrogen Enhance NMR Sensitivity by Polarization Transfer" Science, 323, 1708-1711, (2009).

Golman et al "Real-Time Metabolic Imaging" Proc. Natl. Acad. Sci. USA , 103, 11270-11275 (2006).

Kline , "1H-1H internuclear distance measurements in carbohydrates: proton transient nuclear Overhauser enhancement and spin-lattice relaxation in (13C)- and (2H)-substituted compounds" Canadian Journal of Chemistry, National Research Council Canada :68,Nr:12 : 2171-2182 (1990).

(Continued)

Primary Examiner — Jennifer Lamberski
(74) Attorney, Agent, or Firm — Mark S. Cohen; Pearl Cohen; Zedek Latzer Baratz LLP (57) ABSTRACT

The present invention provides isotopically labeled deoxyglucose and derivatives thereof, methods of their preparation, ration, kits comprising them and uses thereof for spin hyperpolarized magnetic resonance imaging, utilized in the quantitative and qualitative diagnosis of states, conditions, diseases, or disorders in the body of a subject.

10 Claims, 7 Drawing Sheets

(56) References Cited

OTHER PUBLICATIONS

Hayes "Epimerization of Aldoses by Mplybdate Involving a Navel Rearrangement of the Carbon Skeleton" Journal of the American Chemical Society 104,Nr:24 : 6764-6769 (1982).
Nunes "Quantifying Endogenous Glucose Production and Contributing Source Fluxes from a Single 2H NMR Spectrum" Magnetic Resonance in Medicine 62,Nr:3: 802-807 (2009), Wiley-Liss.
Serianni et al "Isotopically-enriched carbohydrates: The Preparation of [2H]-enriched aldoses by catalytic hydrogenolysis of cyanohydrins with 2H21" Canadian Journal of Chemistry, National Research Council Canada . 57, Nr:23 : 3160-3167 (1979).
Avogaro et al "Stable-Label Intravenous Glucose Tolerance Test Minimal Model" Diabetes. ;38(8):1048-55 (Aug. 1989).
Zachwieja et al "Resistance Exercise and Growth Hormone Administration in Older Men: Effects on Insulin Sensitivity and Secretion During a Stable-Label Intravenous Glucose tolerance Test" Metabolism. 45(2):254-60 (Feb. 1996).
Avogaro et al "Epinephrine Exerts Opposite Effects on Peripheral Glucose-Stimulated Insulin Secretion" Diabetes. ;45(10):1373-8 (Oct. 1996).
Hovorka et al "Reproducibility and Comparability of Insulin Sensitivity Indices Measured by Stable-label Intravenous Glucose Tolerance Test" Diabet Med. 15(3):234-46 (Mar. 1998).

\* cited by examiner

ISOTOPICALLY LABELED DEOXY-GLUCOSE AND DERIVATIVES THEREOF, COMPOSITIONS COMPRISING THEM AND USES THEREOF

FIELD OF THE INVENTION

This invention generally relates to isotopically labeled deoxy-glucose and derivatives thereof, and uses thereof for spin hyperpolarized magnetic resonance imaging, for diagnosing of states, conditions, diseases, or disorders.

BACKGROUND OF THE INVENTION

Radioactive fluorinated deoxy-glucose ($^{18}$F-FDG) is being used in medical imaging diagnosis such as positron emission tomography (PET) examinations world-wide. $^{18}$F-FDG emits paired gamma rays, allowing distribution of the tracer to be imaged by external gamma camera(s). This type of diagnostic imaging may be performed in tandem with a CT function which is part of the same PET/CT machine, to allow better localization of small-volume tissue glucose-uptake differences. About 4 million PET scans are performed annually. In these studies, a period of about an hour is given for wash-out of non-specific signals.

The limitations of the PET examination include the use of ionizing radiation and low spatial resolution. This limits the exposure in children and pregnant women and the frequency of repeated exposure for monitoring of therapeutic effects or the relapse/remission cycle of cancer, inflammatory diseases, or neurological conditions.

Yorimitsu et al. have recently shown that a deoxy-glucose analog (having $^{15}$O labeling) has a half life of 2 min and is capable of producing images that show tissue contrast ("Synthesis and Bioimaging of Positron-Emitting $^{15}$O-Labeled 2-Deoxy-D-glucose of Two-Minute Half-Life", *Chem. Asian J.* 2007, 2, 57-65). In this study, regions of high glucose uptake or accumulation such as brain, heart, kidneys, and bladder showed high signal of [$^{15}$O]-DG, with a similar contrast pattern to [$^{18}$F]-FDG in PET. In contrast, $H_2$$^{15}$O administration showed no specific contrast and a uniform distribution of the label in the body.

Both deoxy-glucose and glucose enter tissue cells using specialized proteins called transport proteins that are expressed on the plasma membrane of the cells. The types of transporters that are most efficient in transporting deoxy-glucose and glucose across the plasma membrane are generally called glucose transporters. Glucose transporters can be active or passive. Active transport occurs via co-transporters. This transport of glucose through the apical membrane of intestinal and kidney epithelial cells depends on the presence of secondary active Na+/glucose symporters, SGLT-1 and SGLT-2, which concentrate glucose inside the cells, using the energy provided by co-transport of Na+ ions down their electrochemical gradient. Passive transport of glucose occurs via the GLUTs family of transporters which mediate facilitated diffusion of glucose through the cellular membrane. These glucose carriers (protein symbol GLUT, gene symbol SLC2 for Solute Carrier Family 2) belong to a superfamily of transport facilitators (major facilitator superfamily) including organic anion and cation transporters, yeast hexose transporter, plant hexose/proton symporters, and bacterial sugar/proton symporters. Each glucose transporter isoform plays a specific role in glucose metabolism determined by its pattern of tissue expression, substrate specificity, transport kinetics, and regulated expression in different physiological conditions. The members of the GLUT/SLC2 have been divided into subclasses on the basis of sequence similarities: Class I comprises the well-characterized glucose transporters GLUT1-GLUT4' where GLUT1 has been shown to play a critical role in glucose transport into tumor cells. Class II comprises: GLUT5 (SLC2A5)—a fructose transporter, GLUT7 (SLC2A7), which transports glucose out of the endoplasmic reticulum, GLUT9 (SLC2A9), GLUT11 (SLC2A11). Class III comprises: GLUT6 (SLC2A6), GLUT8 (SLC2A8), GLUT10 (SLC2A10), GLUT12 (SLC2A12), and the H+/myoinositol transporter HMIT (SLC2A13).

The tissue contrast obtained by radioactive deoxy-glucose reflects increased deoxy-glucose uptake, which is known in the art to be due to higher expression of glucose transporters, especially GLUT1. Several deoxy-glucose derivatives such as glucose and glucosamine (e.g. 2-Amino-2-deoxy-D-glucose chitosamine) have similar uptake characteristics ("GLUT2 is a high affinity glucosamine transporter" 2002, FEBS Letters, 524, 199-203) and can therefore serve to produce similar contrast patterns. Also, further glucosamine olefinic derivatives and ester derivatives on the glucose ring show similar uptake and cellular internalization property and may serve to produce similar contrast patterns ("Para-hydrogenated glucose derivatives as potential $^{13}$C-hyperpolarized probes for magnetic resonance imaging", 2010, J Am Chem Soc, 132, 7186-7193).

A previous study in humans using stable isotope labeled glucose 1-[$^{13}$C]glucose and 6,6-[$^{2}$H$_2$]glucose ("$^{13}$C- and $^{2}$H-labelled glucose compared for minimal model estimates of glucose metabolism in man" *Clin. Sci.* 2005, 109, 513-521) used these compounds as means to monitor glucose metabolism. The metabolic products of the labeled analogs were assayed in body fluids by means of gas chromatography combined with mass spectrometry. In another study [1,6-$^{13}$C$_2$]glucose with or without deuterium labeling (D16) was used to monitor glucose metabolism in humans by NMR spectroscopy of blood and urine samples ("Measurement of gluconeogenesis and intermediary metabolism using stable isotopes" 2007, U.S. Pat. No. 7,256,047 B2). 2-deoxy-2-fluoro-D-glucose (FDG) at natural abundance (without stable isotope labeling) had been used to study deoxy-glucose metabolism by $^{19}$F-NMR. The main metabolites found were FDG-6 phosphate (FDG-6-P) and its epimer 2-deoxy-2 fluoro-D-mannose-6 phosphate (FDM-6-P) and their nucleoside-di-phosphate (NDP) forms NDP-FDG and NDP-FDM ("$^{19}$F NMR of 2-Deoxy-2-fluoro-D-glucose for tumor diagnosis in mice. An NDP-bound hexose analog as a new NMR target for imaging" *NMR Biomed.* 1997. 10, 35-41)

Magnetic resonance imaging and spectroscopy (MRI/MRS) has become an attractive diagnosing technique in the last three decades. Due to its non-invasive features and the fact that it does not involve the exposure of the diagnosed patient to potentially harmful ionizing radiation, MRI has become a leading diagnosing imaging procedure implemented in many fields of medicine.

The underlying principle of MRI and MRS is based on the interaction of atomic nuclei with an external magnetic field. Nuclei with spin quantum number I=½ (such as $^{1}$H, $^{13}$C, and $^{15}$N) can be oriented in two possible directions: parallel ("spin up"') or anti-parallel ("spin down") to the external magnetic field. The net magnetization per unit volume, and thus the available nuclear magnetic resonance (NMR) signal, is proportional to the population difference between the two states. If the two populations are equal, their magnetic moments cancel, resulting in zero macroscopic magnetization, and thus no NMR signal. However, under thermal equilibrium conditions, slightly higher energy is associated with the "spin down" direction, and the number of such spins will thus be slightly smaller than the number of spins in the "spin up" state.

An artificial, non-equilibrium distribution of the nuclei can also be created by hyperpolarization NMR techniques for which the spin population differences is increased by several orders of magnitudes compared with the thermal equilibrium conditions. This significantly increases the overall polarization of the nuclei thereby amplifying the magnetic resonance signal intensity.

The enhancement of the hyperpolarized magnetic resonance signal is limited by the relatively fast decay of the hyperpolarization due to spin-lattice relaxation (termed as $T_1$ relaxation time). This decay, combined with the initial level of the hyperpolarized signal, determines the temporal window of ability to detect the hyperpolarized nuclei. Known techniques of enriching the proton positions with deuterium were shown to prolong the $T_1$ relaxation times of carbon-13 in various compounds in a manner that is dependent on the compound's conformation in solution. The prolongation of $T_1$ values is attributed to a decrease in dipolar interaction that a particular nucleus experiences. However, because the dipolar interaction is only one of several relaxation mechanisms that affect the overall $T_1$ relaxation time, it is not possible to predict the extent of this effect for a particular nucleus in specific molecule within a specific medium (for example in the blood). Moreover, prolongation of $T_1$ in itself at times does not allow for practical and effective in vivo magnetic resonance detection of a compound or its metabolic fate when administered to a subject, since the sensitivity of detection is limited due to the low natural abundance of $^{13}C$ nuclei, thereby yielding signals which are below the threshold of detection.

Most spin hyperpolarized MRI studies carried to date and specifically those involving dissolution DNP approach have been focused on metabolic imaging and thereby involved spectroscopic imaging, and the use of a compound that showed a chemical shift difference between its substrate form to its metabolic product.

There is a need in the field of the invention to provide non-radioactive glucose compounds capable of providing a clear, quick, and safe diagnostic tool for different states, conditions, and disorders using magnetic resonance imaging, based only on the distribution or the uptake process of these compounds.

It is known in the art that the glucose tolerance test consists of a bolus injection of a high glucose dose of 0.5 g/Kg (approximately 35 g for an average person weighing 70 Kg). The acute toxicity of intravenous injected 2-deoxy-D-glucose (2DG) was investigated in rats. No death was reported at a dose of 0.25, 0.5, and 1 g/Kg. In these doses, there was no change in heart rate or respiratory rate, but there was a mean decrease in arterial blood pressure at these doses, but not in a dose dependent manner ("Acute toxicity and cardio-respiratory effects of 2-Deoxy-D-Glucose: A promising radio sensitiser" *Biomed. Environ. Sci.* 2006, 19, 96-103). However, it is known in the art that molecular imaging is based on low dose administration of contrast media, whether at a nanomol level in PET examination or below 1 mmol/Kg in hyperpolarized magnetic resonance studies. The rational for this low dosing approach is 1) safety—to avoid adverse effects, and 2) the need to perturb the physiology as little as possible, as uptake and metabolism are dependent on substrate concentration.

The ability of a compound to serve as contrast media on hyperpolarized MRI is dependent to a great extent on the $T_1$ of its relevant $^{13}C$ nucleus or nuclei. The $T_1$ of glucose carbon-13 nuclei was recently found to be less than 2 s at 600 MHz in a hyperpolarized state ("Selection of endogenous $^{13}C$ substrates for observation of intracellular metabolism using the dynamic nuclear polarization technique" *Jpn. J. Radiol.* 2010, 28(2), 173-9) and it was concluded that glucose is not suitable for use with the DNP technique.

Therefore, there is a need in the medical imaging field for a non-radioactive imaging agent that will produce tissue contrast that is similar to that of deoxy-glucose when used as $^{18}F$-FDG in PET examinations, thereby enabling non-radioactive imaging of different diseases such as for example oncologic, neurologic, psychiatric, and inflammatory processes. In addition, there is a need for a high signal imaging agent per se that does not utilize ionizing radiation, for imaging of blood vessels and vasculature to enable hyperpolarized MR angiography or catheter angiography.

SUMMARY OF THE INVENTION

In one of its aspects the present invention provides deoxy-glucose comprising at least one isotopically labeled carbon atom directly bonded to at least one deuterium atom (commonly marked as D or $^2H$). In a further aspect the invention provides deoxy-glucose consisting of at least one isotopically labeled carbon atom directly bonded to at least one deuterium atom.

In some embodiments said deoxy-glucose comprises two isotopically labeled carbon atoms each directly bonded to at least one deuterium atom.

In other embodiments, said deoxy-glucose comprises 1 to 6 isotopically labeled carbon atoms each directly bonded to at least one deuterium atom.

In some other embodiments, said isotopically labeled carbon atom is $^{13}C$. In other embodiments said isotopically labeled carbon atom is an $sp^3$ carbon atom (i.e. has an $sp^3$ hybridization, therefore is connected to neighboring atoms via sigma bonds). In other embodiments, said isotopically labeled carbon atom is an $sp^2$ carbon atom (i.e. has an $sp^2$ hybridization, therefore is connected to neighboring atoms via at least one pi bond).

When referring to a deoxy-glucose molecule, it should be understood to encompass any isomer (including any natural or synthetic structural isomer, any natural or synthetic stereochemical isomer or any natural or synthetic conformational isomer) of a glucose molecule wherein one of its hydroxy groups is replaced by hydrogen. Therefore, when referring to deoxy-glucose the invention encompasses any one of the following isomers: 2-deoxy-glucose, 3-deoxy glucose, 4-deoxy glucose or 6-deoxy-glucose. The present invention relates to any structural isomer of deoxy-glucose, being in a cyclic hemiacetal form or the linear aldohexose form of deoxy-glucose. Furthermore, the invention relates to all possible stereoisomers of deoxy-glucose (either in the cyclic or linear form, including D-deoxy-glucose and L-deoxy-glucose and all possible enantiomers and diastereomers in the cyclic and linear forms) and to all possible anomers of deoxy-glucose (α-deoxy-glucose or β-deoxy-glucose).

In some embodiments, a derivative of deoxy-glucose is glucose. When referring to glucose, it should be understood to encompass any isomer (including any natural or synthetic structural isomer, any natural or synthetic stereochemical isomer or any natural or synthetic conformational isomer) of 6-(hydroxymethyl)oxane-2,3,4,5-tetrol. The present invention relates to any structural isomer of glucose, being in a cyclic hemiacetal form or the linear aldohexose form of glucose. Furthermore, the invention relates to all possible stereoisomers of glucose (either in the cyclic or linear form, including D-glucose and L-glucose and all possible enantiomers and diastereomers in the cyclic and linear forms) and to all possible anomers of glucose (α-glucose or β-glucose).

The term "isotopically labeled atom" is meant to encompass an atom in a compound of the invention for which at least one of its nuclei has an atomic mass which is different than the atomic mass of the prevalent naturally abundant isotope of the same atom. Due to different number of neutrons in the nuclei, the atomic mass of isotopically labeled atoms is different. The total number of neutrons and protons in the nucleus represents its isotopic number.

In some embodiments an isotopically labeled atom is $^{13}C$ (having 7 neutrons and 6 protons in carbon nucleus). In other embodiments an isotopically labeled atom is $^{2}H$ (having 1 neutron and 1 proton in hydrogen nucleus). In further embodiments, a deoxy-glucose derivative may be labeled with $^{19}F$ (having 10 neutrons and 9 protons in fluorine nucleus) which is 100% naturally abundant, or with $^{18}F$ (having 9 neutrons and 9 protons in fluorine nucleus) which is a radionuclide that is used in combination with PET. As will be appreciated by the description below, the isotopic labeling of specific atoms in a compound of the invention is achieved by techniques known to a person skilled in the art of the invention, such as for example synthesizing compounds of the invention from isotopically labeled reactants or isotopically enriching specific nuclei of a glucose molecule or any metabolite or derivative thereof.

When referring to a deoxy-glucose and/or glucose molecule or any metabolite or derivative thereof comprising at least one isotopically labeled atom, it should be understood to encompass compounds having isotopically labeled atoms above the natural abundance of said at least one isotopically labeled atom. Thus, in some embodiments when said isotopically labeled atom is deuterium, said isotopical enrichment of said deuterium in a specific position in a compound of the invention, may be between about 0.015% to about 99.9%. Thus, in other embodiments when said isotopically labeled atom is $^{13}C$, said isotopical enrichment of said carbon in a specific position in a compound of the invention, may be between about 1.1% to about 99.9%. Thus, in some other embodiments when said isotopically labeled atom is $^{18}F$, said isotopical enrichment of said fluorine in a specific position in a compound of the invention, may be in between about 0.001% to about 100%. Thus, a compound or a composition of the invention may have different degrees of enrichment of isotopically labeled atoms.

In further embodiments, said deoxy-glucose of the invention has $T_1$ relaxation time values of $^{13}C$ nuclei of between about 2 to about 60 sec.

In other embodiments, said deoxy-glucose of the invention further comprises at least one isotopically labeled hydrogen atom. In other embodiments, said deoxy-glucose of the invention, further comprises at least one isotopically labeled carbon atom. In further embodiments of the invention, said deoxy-glucose and/or glucose molecule or any metabolite or derivative thereof further comprising at least one isotopically labeled hydrogen atom. In other embodiments, said deoxy-glucose and/or glucose molecule or any metabolite or derivative thereof further comprising at least one isotopically labeled carbon atom. In other embodiments, said deoxy-glucose molecule or any metabolite or derivative thereof, further comprises at least one isotopically labeled fluorine atom.

In other embodiments a deoxy-glucose and/or glucose molecule or any metabolite or derivative thereof of the invention further comprises at least one additional isotopically labeled carbon atom. In some embodiments said at least one additional isotopically labeled carbon atom may be directly bonded to said at least one isotopically labeled carbon atom. In other embodiments said at least one additional isotopically labeled carbon atom may be adjacent to said at least one isotopically labeled carbon atom.

In yet further embodiments of the invention said deoxy-glucose and/or glucose molecule or any metabolite or derivative thereof further comprise at least one additional isotopically labeled hydrogen atom. In some embodiments said at least one additional isotopically labeled hydrogen atom may be bonded to at least one adjacent to said at least one isotopically labeled carbon atom.

In some embodiments said deoxy-glucose and derivative of the invention are selected from the following list: [$^{13}C_6$, $^{2}H_8$]deoxy-glucose, [1-$^{13}C$, 1-$^{2}H$]deoxy-glucose, [1-$^{13}C$, 1-$^{2}H$]deoxy-glucose, [2-$^{13}C$, 2-$^{2}H$]deoxy-glucose, [3-$^{13}C$, 3-$^{2}H$]deoxy-glucose, [4-$^{13}C$, 4-$^{2}H$]deoxy-glucose, [5-$^{13}C$, 5-$^{2}H$]deoxy-glucose, [6-$^{13}C$, 6-$^{2}H$]deoxy-glucose, [1-$^{13}C$, 1,1-$^{2}H_2$]-1-deoxy-glucose, [2-$^{13}C$, 2,2-$^{2}H_2$]-2-deoxy-glucose, [3-$^{13}C$, 3,3-$^{2}H_2$]-3-deoxy- glucose, [4-$^{13}C$, 4,4-$^{2}H_2$]-4-deoxy-glucose, [5-$^{13}C$, 5,5-$^{2}H_2$]-5-deoxy-glucose, [6-$^{13}C$, 6,6-$^{2}H_2$]-6-deoxy-glucose, [6-$^{13}C$, 6,6,6-$^{2}H_3$]-6-deoxy-glucose, and any deoxy-glucose molecule in which carbon positions 1-6 maybe labeled with $^{13}C$ and any of the protons directly bonded to these carbon positions maybe isotopically labeled with $^{2}H$ and any combinations or permutations thereof;

In further embodiments of the invention, said deoxy-glucose derivative may be selected from: [$^{13}C_6$, $^{2}H_7$]-glucose, [1-$^{13}C$, 1-$^{2}H$]-glucose, [1-$^{13}C$, 1-$^{2}H$]-glucose, [2-$^{13}C$, 2-$^{2}H$]-glucose, [3-$^{13}C$, 3-$^{2}H$]-glucose, [4-$^{13}C$, 4-$^{2}H$]-glucose, [5-$^{13}C$, 5-$^{2}H$]-glucose, [6-$^{13}C$, 6-$^{2}H$]-glucose, [1-$^{13}C$, 1,1-$^{2}H_2$]-1-glucose, [2-$^{13}C$, 2,2-$^{2}H_2$]-2-glucose, [3-$^{13}C$, 3,3-$^{2}H_2$]-3-glucose, [4-$^{13}C$, 4,4-$^{2}H_2$]-4-glucose, [5-$^{13}C$, 5,5-$^{2}H_2$]-5-glucose, [6-$^{13}C$, 6,6-$^{2}H_2$]-6-glucose, [6-$^{13}C$, 6,6,6-$^{2}H_3$]-6-glucose, and any glucose molecule in which carbon positions 1-6 maybe labeled with $^{13}C$ and any of the protons directly bonded to these carbon positions maybe isotopically labeled with $^{2}H$ and any combinations or permutations thereof.

In other embodiments said deoxy-glucose and/or derivative thereof is in a hyperpolarized state. In some embodiments, hyperpolarization of said deoxy-glucose and/or derivatives thereof is achieved using dynamic nuclear polarization technique or para-hydrogen induced polarization.

In a further aspect the invention provides a composition comprising at least one deoxy-glucose and/or derivative thereof, according to the invention.

In yet a further aspect the invention provides deoxy-glucose, according to any one of the embodiments of the invention or any derivative thereof, for use in diagnosing and evaluating a condition or disease.

In some embodiments of a use of the invention, said derivative of a deoxy-glucose of the invention is glucose having at least one isotopically labeled carbon atom directly bonded to at least one deuterium atom.

In some embodiments said glucose comprises two isotopically labeled carbon atoms each directly bonded to at least one deuterium atom. In other embodiments, said glucose comprises 1 to 6 isotopically labeled carbon atoms each directly bonded to at least one deuterium atom. In further embodiments, a glucose molecule of the invention may be labeled with $^{19}F$ (having 10 neutrons and 9 protons in fluorine nucleus) which is 100% naturally abundant, or with $^{18}F$ (having 9 neutrons and 9 protons in fluorine nucleus) which is a radionuclide that is used in combination with PET. In other embodiments, said glucose of the invention further comprises at least one isotopically labeled hydrogen atom. In other embodiments, said glucose of the invention, further comprises at least one isotopically labeled carbon atom. In further embodiments of the invention, said glucose molecule of the invention further comprises at least one isotopically labeled hydrogen atom. In other embodiments, said glucose further comprises at least one isotopically labeled carbon atom. In other embodiments, said glucose, further comprises at least one isotopically labeled fluorine atom.

In other embodiments a glucose molecule of the invention further comprises at least one additional isotopically labeled carbon atom. In some embodiments said at least one additional isotopically labeled carbon atom may be directly bonded to said at least one isotopically labeled carbon atom. In other embodiments said at least one additional isotopically labeled carbon atom may be adjacent to said at least one isotopically labeled carbon atom. In yet further embodiments of the invention said glucose molecule or any further comprise at least one additional isotopically labeled hydrogen atom. In some embodiments said at least one additional isotopically labeled hydrogen atom may be bonded to at least one adjacent to said at least one isotopically labeled carbon atom.

In other embodiments of the invention said diagnosis and/or evaluation of a state, condition, or disease is based on first pass or uptake imaging.

When referring to diagnosis and/or evaluation of a state, condition, or disease that is based on first pass imaging it should be understood to encompass the distribution of a hyperpolarized compound of the invention (contrast agent providing the hyperpolarized signal) in a short time frame, in some embodiments of up to 30 seconds from the moment of administration, which is shorter than the time for re-circulation, i.e. before a hyperpolarized compound of the invention (contrast agent) had reached the site of injection or an organ of target for the second time via the blood circulation through the vasculature. Any time shorter than the re-circulation time is considered first pass imaging time. For example, re-circulation of a hyperpolarized compound of the invention (contrast agent) in the brain may be visible by a second contrast peak in the brain region, when consecutive images of the brain are acquired following contrast media administration.

When referring to diagnosis and/or evaluation of a state, condition, or disease that is based on uptake it should be understood to encompass the distribution of the hyperpolarized compound of the invention (contrast agent providing the hyperpolarized signal) in the tissue of interest and surrounding tissues at any given time post administration when the signal is visible as measured by non-metabolic imaging of said deoxy-glucose and/or glucose molecule or any metabolite or derivative thereof. The differences in the signal distribution between tissues, or the tissue contrast, emanates from different uptake rates into the tissue cells where these rates of uptake or accumulation are determined by the type of transporters expressed on the tissue cell plasma membranes, on the number of these transporters in each cell, as well as on the particular cellular density. Tissue imaging of hyperpolarized deoxy-glucose or glucose uptake can be acquired for as long as the hyperpolarized signal is visible and higher than the measurement noise. The time frame for such imaging is 2 seconds to 1 to 2 minutes post-injection of the contrast media.

In yet further embodiments, said diagnosis and/or evaluation of a condition or disease is based on the uptake of deoxy-glucose of the invention or glucose of the invention.

As noted above in order to acquire an NMR signal of a particular nucleus of a compound there has to be a significant difference between the spin population energy levels of said nucleus. The strength of the NMR signal is linearly dependent on the number of nuclei at the low energy level. The difference between the population of a nucleus at high and low nuclear energy levels is the "polarization" of the nuclei, which is defined as $P=CB_0/T$, where C is a nucleus specific constant, $B_0$ is the magnetic field strength, and T is the absolute temperature. Under thermal equilibrium conditions, the polarization is relatively low thereby resulting in a very weak signal under standard clinical MRI scanners (at body temperature of about 37° C. for a magnetic field of 1.5 T, P (for $^1$H) is approximately $5\times10^{-6}$ and P (for $^{13}$C) is approximately $1\times10^{-6}$).

In order to increase the polarization of a specific nucleus in a compound consequently creating an artificial, non-equilibrium distribution of the spin population of a nucleus, i.e. a "hyperpolarized" state, where the spin population difference is increased by several orders of magnitudes compared with the thermal equilibrium, the technology of ex vivo hyperpolarization by means of dynamic nuclear polarization (DNP) techniques, such as the Overhauser effect, in combination with a suitable free radical (e.g. TEMPO and its derivatives). Hyperpolarization may also be performed ex-vivo using the Para-hydrogen Induced Polarization technique, and ortho-deuterium induced polarization. Ex-vivo hyperpolarization may also be performed by interaction with a metal complex and reversible interaction with para-hydrogen without hydrogenation of the organic molecule. These techniques have been described in U.S. Pat. Nos. 6,466,814, 6,574,495, and 6,574,496, and in Adams R. W. et al. (Science, 323, 1708-1711, 2009), the contents of which are incorporated herein by reference.

Ex vivo hyperpolarization of a compound of the invention is performed in order to reach a level of polarization sufficient to allow a diagnostically effective contrast enhancement of said agent. In some embodiments, said level of hyperpolarization may be at least about a factor of 2 above the thermal equilibrium polarization level at the magnetic field strength at which the MRI is performed. In some embodiments, said level of hyperpolarization is at least about a factor of 10 above the thermal equilibrium polarization level at the magnetic field strength at which the MRI is performed. In other embodiments, said level of hyperpolarization is at least about a factor of 100 above the thermal equilibrium polarization level at the magnetic field strength at which the MRI is performed. In yet further embodiments, said level of hyperpolarization is a factor of at least about 1000 above the thermal equilibrium polarization level at the magnetic field strength at which the MRI is performed. In other embodiments said level of hyperpolarization is a factor of at least about 10000 above the thermal equilibrium polarization level at the magnetic field strength at which the MRI is performed. In further embodiments said level of hyperpolarization is a factor of at least 100000 above the thermal equilibrium polarization level at the magnetic field strength at which the MRI is performed.

A hyperpolarized deoxy-glucose and/or glucose molecule or any metabolite or derivative thereof according to the invention comprises nuclei capable of emitting magnetic resonance signals in a magnetic field (e.g. nuclei such as $^{13}$C) and capable of exhibiting $T_1$ relaxation times between about 1 to about 60 sec (at standard MRI conditions such as for example at a field strength of 0.01-5T and a temperature in the range 20-40° C.). In some embodiments, said hyperpolarized deoxy-glucose and/or glucose molecule or any metabolite or derivative thereof according to the invention has $T_2$ relaxation times of $^{13}C$ nucleus of between about 10 to about 10,000 msec.

In some embodiments, said state, condition, or disease diagnosed and/or evaluated using a deoxy-glucose and glucose of the invention is selected from:

Oncologic related states, diseases or conditions including but not limited to: Tumor staging and differentiation, tumor grading, determination of tumor penetration into surrounding tissue, monitoring response to treatment, distant metastases, systemic metastasis, lymph node staging, recurrent disease, cancer imaging, radiation oncology, central nervous system tumors and cancer, head and neck cancer, brain cancer, thyroid cancer and thyroid imaging, anaplastic carcinomas of thyroid, lung cancer, non-small cell lung cancer, lymphoma and myeloma, malignant melanoma, breast cancer, esophageal cancer, colorectal carcinoma, pancreatic and hepatobiliary cancer, gynecological tumors, cervical and uterine cancers, ovarian cancer, endometrial cancer, genitourinary malignancies, sarcomas, gastrointestinal stromal tumors, neuroendocrine tumors, gastrinoma, glomus tumor, liver metastasis, astrocytoma, pilocytic astrocytoma, glioblastoma, carcinoma of unknown primary including paraneoplastic neurological syndromes, carcinoid tumor, cancer in pediatric patients, gallbladder carcinoma, hypoxia imaging, angiogenesis imaging, antiangiogenic therapeutic strategies, lymph node metastasis, Breslow's depth and thickness determination, bone lesions, bladder cancer, brown fat and hibernoma, cholangiocarcinomas, pulmonary node detection, ganglioglioma, gliomatosis cerebri, malignant degeneration of low grade glioma, prostate cancer, renal cancer, testicular cancer, genitourinary tract cancer, kidney cancer, hepatobiliary tumors, benign tumors—adrenal adenoma, and adrenal hypertrophy;

Neurologic related states, diseases or conditions including but not limited to: movement disorders, stroke, epilepsy, epilepsy in childhood, extratemporal lobe epilepsy, dementia, amphetamine induced activity, Alzheimer's disease, early onset familial Alzheimer's disease, cerebral amyloid angiopathy, dementia with Lewy bodies, frontotemporal lobal degeneration, mild cognitive impairment, Parkinson's disease, atypical parkinsonian disorders, brain development, central nervous system tumors, cerebral blood flow, interictal imaging, ictal imaging, infantile spasms, Lennox-Gastaut syndrome, normal aging imaging, cerebral oxygen metabolism, stroke, corticobasal degeneration, frontal hypometabolism, and Gilles de la Tourette syndrome;

Psychiatric related states, diseases or conditions including but not limited to: affective disorders, bipolar disorder, depression, major depressive disorder, alcohol abuse, substance abuse, cocaine abuse, anxiety disorders, personality disorders, schizophrenia, schizoaffective disorder, social fobia, post-traumatic stress disorder, and obsessive compulsive disorder;

Cardiac and vascular related states, diseases or conditions including but not limited to: evaluation of myocardial perfusion, myocardial viability, oxidative metabolism and cardiac efficiency, hypertension, myocardial neurotransmitter imaging, absolute myocardial blood flow assessment, congestive heart failure, aortic graft, arterial plasma measurement, atherosclerosis, blood vessel formation, cardiac resynchronization assessment, coronary artery disease assessment, coronary viability assessment, myocardial involvement in endocrine disorders, cardiac stem cell therapy, cardiomyopathy, pediatric cardiology, dilated cardiomyopathy, myocardial reserve assessment, dobutamine stress test, heart innervations, heart transplantation, valvular heart disease, ischemic myocardium, imaging the neovasculature, imaging of blood volume and vascular permeability;

Infection and inflammation related states, diseases or conditions including but not limited to: infection in pediatric patients, cardiorespiratory infectious processes, fever of unknown origin, focal soft tissue infections, foreign body inflammatory reaction, infection and inflammation in immune compromised patients, infection superimposed on malignancy, inflammation in children, inflammatory bowel disease (IBD), colitis, Crohn's disease, musculoskeletal inflammatory process, inflammatory joint disease, joint prosthesis infection, metallic implant infection, osteomyelitis, sarcoidosis, vascular infection, vascular graft infection, vasculitis, vulnerable atherosclerotic plaque, rheumatoid arthritis, systemic and local autoimmune diseases, AIDS infection, differentiating inflammation from malignancy, pyogenic infection, parasitic, viral infection, and bacterial infection;

Kidneys related states, diseases or conditions including but not limited to: Alport syndrome, renography, captopril renography, renal artery stenosis, and kidney transplantation;

General states, diseases or conditions including but not limited to: mapping and/or monitoring over time of abnormal metabolism, mapping of metabolic response to extrinsic or intrinsic modulation, angiography, catheter angiography, interventional radiology, neuro-interventional radiology, hemorrhagic infarction, head injuries, brain trauma conditions, and hemorrhagic stroke.

In other embodiments, said deoxy-glucose and/or any derivatives and/or metabolites thereof according to the invention may be used in drug development and therapeutic monitoring applications, which may include but are not limited to: anticancer agents, anti-angiogenic therapeutic strategies, treatment plan, determination of tumor response to treatment and medication effects, growth factor antagonists and endothelial cell signal transduction inhibitors, integrin activation inhibitors, matrix metalloproteinase inhibitors, antihypertensive therapy, anti-infective drug delivery, antioxidant therapy for smokers, antipsychotics, antipsychotics for schizophrenia, drug occupancy studies, antiapoptotic drugs, evaluation of aerobic and anaerobic glycolosis, early response determination, evaluation of post-treatment remission, pharmacokinetics evaluation, bioreductive drugs, endothelial cell proliferation inhibitors, endothelial cell signal transduction inhibitors, anti-infective drugs, and gene therapy assessment;

In some embodiments, said state, condition, or disease diagnosed and/or evaluated using a deoxy-glucose and glucose of the invention where the biomarker includes either higher or lower uptake than surrounding tissue. For example, malignant lesions are characterized by higher uptake, however, epileptic foci in the brain after seizure and area of low or null perfusion in the myocardium are characterized by lower uptake than surrounding normal counterpart tissue.

In a further aspect the invention provides a use of deoxy-glucose of the invention, and/or any derivative thereof (for example glucose according to the invention) for the manufacture of a composition for diagnosing and evaluating a condition or disease.

In other embodiments of a use of the invention said diagnosing and evaluating of a state, condition, or disease is performed using uptake, non-metabolic imaging of said glucose molecule or any metabolite or derivative thereof.

In further embodiments of a use of the invention, said deoxy-glucose derivative is glucose having at least one isotopically labeled carbon atom directly bonded to at least one deuterium atom.

In further embodiments of a use of the invention, said composition comprises said deoxy-glucose or derivative thereof in an amount of between about 0.005 g/Kg to about 0.5 g/Kg.

In another one of its aspects the invention provides a method for diagnosing and evaluating a condition or disease in a subject, said method comprising:
  hyperpolarizing at least one deoxy-glucose or any derivative thereof according to the invention;
  administering to said subject an effective amount of hyperpolarized at least one deoxy-glucose or any derivative thereof;
  imaging the distribution of said hyperpolarized at least one deoxy-glucose or any derivative thereof;
  thereby diagnosing said condition or disease.

In some embodiments of a method of the invention, said monitoring is performed by means of magnetic resonance imaging.

In other embodiments of a method of the invention said effective amount of hyperpolarized at least one deoxy-glucose or any derivative thereof is between about 0.005 g/Kg to about 0.5 g/Kg.

In other embodiments of a method of the invention said subject is administered with consecutive doses of said hyperpolarized deoxy-glucose or any derivative thereof.

In further embodiments of a method of the invention, said hyperpolarization is performed using dynamic nuclear polarization techniques or para-hydrogen induced polarization techniques.

In other embodiments of a method of the invention, said diagnosis and evaluation is performed during or after said subject is administered with at least one therapeutic agent.

In further embodiments of a method of the invention, said diagnosis and evaluation of said condition or disease involves a non-metabolic imaging of said deoxy-glucose or any derivative thereof.

In other embodiments of a method of the invention, said state condition or disease is selected from Oncologic applications, Neurologic applications, Psychiatric disorders, Cardiac and vascular applications, Infection and inflammation applications, Drug development and therapeutic monitoring applications, Kidneys applications, and General applications, as provided in detail above.

In yet further embodiments of a method of the invention said deoxy-glucose derivative is glucose having at least one isotopically labeled carbon atom directly bonded to at least one deuterium atom.

The invention further provides a kit comprising at least one component containing at least one deoxy-glucose or any derivative thereof comprising at least one isotopically labeled carbon atom directly bonded to at least one deuterium atom, means for administering said at least one deoxy-glucose or any derivative thereof and instructions for use. In some embodiments a kit of the invention is intended for use in diagnosing and evaluating a condition or disease.

In further embodiments, a composition of the invention further comprises at least one additional (different) deoxy-glucose and/or glucose molecule or any metabolite or derivative thereof according to the invention. In another embodiment, a composition of the invention further comprises at least one fluorinated deoxy-glucose and/or glucose molecule or any metabolite or derivative thereof. In other embodiments, said fluorinated deoxy-glucose and/or glucose molecule or any metabolite or derivative thereof is labeled with $^{18}F$.

It is noted that said composition may comprise at least one deoxy-glucose and/or glucose molecule or any metabolite or derivative thereof according to the invention in a mixture with pharmaceutically acceptable auxiliaries, and optionally other therapeutic agents. The auxiliaries must be "acceptable" in the sense of being compatible with the other ingredients of the composition and not deleterious to the recipients thereof.

Compositions administrable to a subject include those suitable for oral, rectal, nasal, topical (including transdermal, buccal, and sublingual), vaginal or parenteral (including subcutaneous, intramuscular, intravenous, and intradermal) administration or administration via an implant. The compositions may be prepared by any method well known in the art of pharmacy. Such methods include the step of bringing in association a deoxy-glucose and/or glucose molecule or any metabolite or derivative thereof the invention with any auxiliary agent. The auxiliary agent(s), also named accessory ingredient(s), include those conventional in the art, such as carriers, fillers, binders, diluents, disintegrants, lubricants, colorants, flavoring agents, anti-oxidants, and wetting agents.

Compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

The invention further includes a composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilized) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulizers or insufflators.

The compounds of the invention may be administered in conjunction with other compounds, including, but not limited to physiological saline and buffers, radical residues, minute amounts of Gd-chelates such as Gd-DTPA, Gd-DOTA, Gd-EDTA, minute amount of biocompatible DNP glassing agents such as ethanol and glycerol, and other hyperpolarized compounds such as choline and pyruvate.

In some embodiments, a state, condition, or disease diagnosed and/or evaluated using a composition of the invention is selected from Oncologic applications, Neurologic applications, Psychiatric disorders, Cardiac and vascular applications, Infection and inflammation applications, Drug development and therapeutic monitoring applications, Kidneys applications, and General applications, as provided in detail above.

Additional conditions and diseases that may be diagnosed and evaluated using a method and/or composition of the invention include those commonly known to be diagnosed and evaluated using FDG-PET techniques such as for example cancer tumors. Is should be noted that since the uses and methods of the invention do not involve the use of and exposure of the subject to radioactive ionization, it is possible to use the methods and uses of the present invention in order to diagnose and evaluate states, conditions, and diseases in other populations that are usually not commonly examined by FDG-PET, such as for example children and pregnant women. Furthermore, it is possible to perform repeated examinations within a short time frame (more than 1 examination per day), fetal examinations, placental viability/perfusion examinations, repeated examination of relapse/remission cycle of inflammatory diseases such as rheumatoid arthritis and Crohn's disease, and myocardial viability examination—where specifically desired is a single examination where it is possible to image 1) cardiac output, 2) coronary angiography, and 3) perfusion. The latter may replace the CT angiography examination which is associated with high radiation doses.

Additional examinations include angiography and catheter angiography. It can be shown that hyperpolarized isotopically labeled deoxy-glucose and/or glucose of the invention can be injected at a concentration of ca. 300 mM in blood with a polarization enhancement factor of at least 1,000 for each of the 6 carbon-13, thus at a field of 3 T the expected signal level in the vasculature can reach 1980 M*ppm (taking into account 0.3 M, thermal polarization for $^{13}$C of about 1.1 ppm, enhancement factor of 1,000, and 6 carbons per molecule). In comparison the signal level of Gd-enhanced angiography is only 990 M*ppm (taking into account 110 M concentration of water in water as an upper limit for the concentration of water in blood, thermal polarization for $^1$H of 4.5 ppm, and 2 protons per molecule). This higher signal is also accompanied by the lack of background signal in the hyperpolarized application compared to the Gd-enhanced proton-MRI angiography, which is expected to enable higher resolution and/or faster angiographic MRI applications. This presents an alternative to X-ray or CT angiography which is associated with high radiation doses for the patients, technicians, and physicians.

These applications of MRI using hyperpolarized deoxy-glucose and/or glucose of the invention, by providing an alternative to FDG-PET also reduce the need for hybrid imaging systems such as PET-CT scanners and PET-MRI scanners because the entire anatomical imaging examination and the functional/uptake/distribution examination can be performed in a conventional MRI scanner equipped with $^{13}$C compatible hardware; this is likely to reduce the cost of such medical imaging applications.

FDG-PET had been shown to provide diagnostic benefit to neurodegenerative diseases such as Alzheimer's disease and Parkinson's disease, however these applications are limited by the low spatial resolution of PET. MRI using hyperpolarized deoxy-glucose and/or glucose of the invention presents a means to perform similar diagnostic evaluations at higher spatial resolution and no ionizing radiation.

The use of strictly $^{13}$C imaging as opposed to spectroscopic imaging which is usually performed in metabolic studies provides a relative increase in SNR and lowers the requirements placed on pulse sequence and reconstruction tools.

The term "diagnosing and evaluating a state, condition, or disease" is meant to encompass any process of investigating, identifying, recognizing and assessing a state, condition, disease, or disorder of the mammalian body (including its brain). A diagnosis according to the present invention using a deoxy-glucose and/or glucose molecule or any metabolite or derivative thereof according to the invention includes, but is not limited to the objective quantitative diagnosis of a condition or disease, prognosis of a condition or disease, genetic predisposition of a subject to have a condition or disease, efficacy of treatment of a therapeutic agent administered to a subject (either continually or intermittently), quantification of neuronal function, diagnosis and evaluation of a psychiatric, neurodegenerative, and neurochemical diseases and disorders, affirmation of a therapeutic agent activity, determination of drug efficacy, characterization of masses, tumors, cysts, blood vessel abnormalities, and internal organ function; quantification of brain, kidney, liver, and other organs' function; evaluation and determination of the level of anesthesia, comatose states, and the brain regions affected by stroke or trauma and their penumbra, kidney, liver, and muscle function, examination of the action, response or progress of therapy (involving medicinal and non-medicinal treatment) aimed at alleviating or curing psychiatric and neurodegenerative diseases and disorders.

The term "monitoring" as used herein is meant to encompass the quantitative and/or qualitative detection and observation of a hyperpolarized deoxy-glucose and/or glucose or any metabolite or derivative thereof according to the invention administered to said subject. Monitoring may be performed by any non-invasive or invasive imaging method, including, but not-limited to magnetic resonance spectroscopy, magnetic resonance imaging, magnetic resonance spectroscopic imaging, and PET.

In other embodiments, said magnetic resonance spectroscopy is performed using a double tuned $^{13}$C/D RF coil. Due to possible coupling between deuterium nuclei and $^{13}$C-nucleus, the signals $^{13}$C-signals are split, their intensity is diminished and the signal width is broadened. In order to allow visibility of the agent's or its metabolite's signals it is sometimes necessary to improve on the line-width of this signal and increase its intensity. This may be achieved by using a double tuned $^{13}$C/$^2$H RF coil or another combination of such coils that is capable of performing deuterium decoupling during the $^{13}$C acquisition. Various coil design possibilities such as a saddle coil, a birdcage coil, a surface coil, or combinations thereof are suitable for this purpose.

DETAILED DESCRIPTION OF EMBODIMENTS

In order to understand the invention and to see how it may be carried out in practice, embodiments will now be described, by way of non-limiting example only, with reference to the accompanying drawings.

The clinical diagnosis based on the uptake of hyperpolarized deoxy-glucose or glucose relies to a significant extent on "first pass" and uptake, due to the short term of exposure to the contrast media prior to imaging (approximately 30-60 s). This term encompasses both uptake rate at specific tissues as well as the flow rate to the tissue. High flow rate contributes to the accumulation of glucose signal in a tissue.

Figure 2:
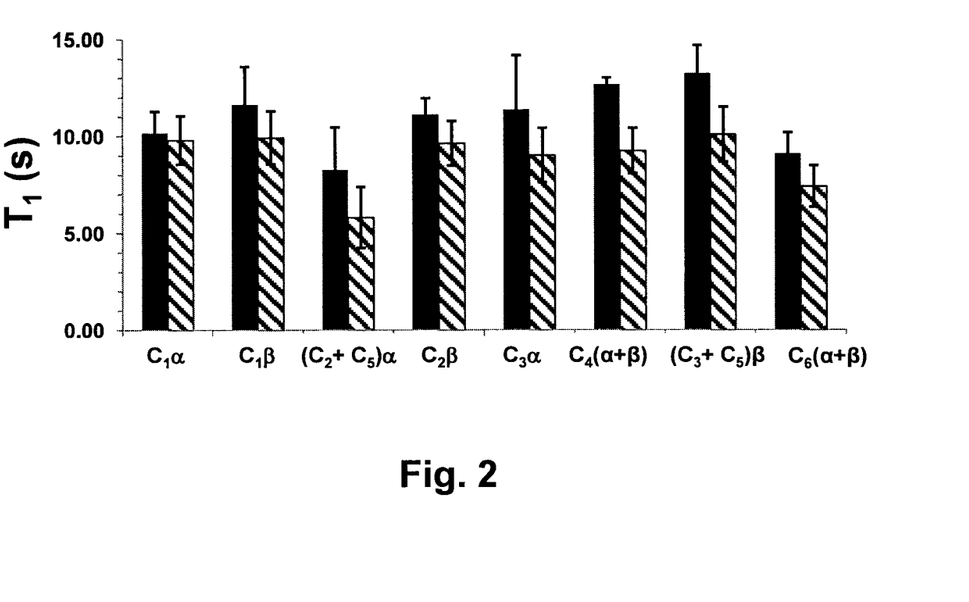
FIG. 2 shows the effect of the magnetic field strength on the $T_1$ of glucose carbons.
Figure 3:
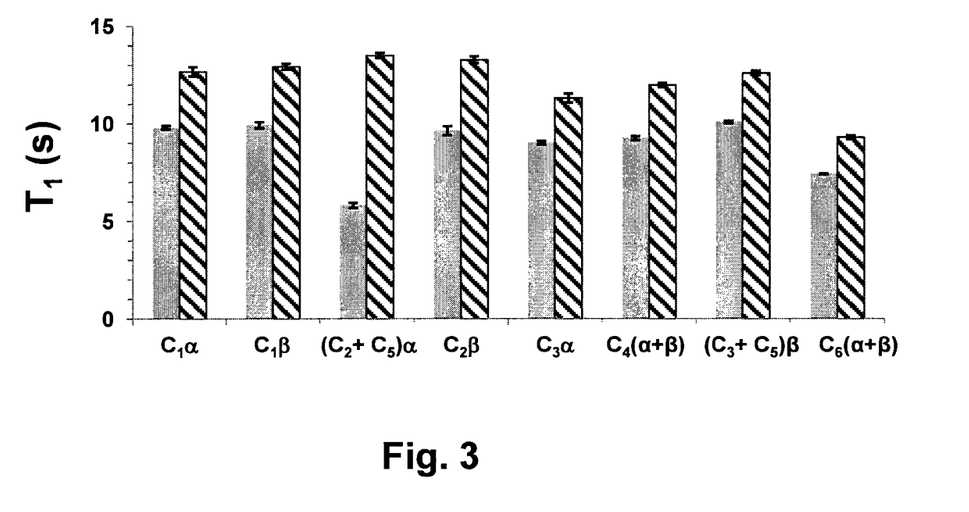
FIG. 3 shows the effect of direct bonding between carbon-13s on each other's $T_1$ in the glucose molecule.

The effect of glucose concentration on the $T_1$ of its carbon positions was investigated at 7 T (FIG. 1A) and at 11.8 T (FIG. 1B) using Varian NMR spectrometers (The Netherlands). [U-$^{13}C_6$, $^2H_7$]glucose was obtained from Cambridge Isotopes Laboratories (Andover, Mass., USA). The $T_1$ of [U-$^{13}C_6$, $^2H_7$]glucose $^{13}$C's was measured using the inversion recovery pulse sequence. The $T_1$ of glucose carbons was found to be longer in a physiological compatible solution (400 mM, solid gray columns) compared to a concentrated solution (4.03 M, diagonal pattern columns). The mean difference between the $T_1$s of the two concentrations was 6.9 s (P=2*10$^{-6}$, paired t-test) at 7 T. The mean difference in $T_1$ at 11.8 T was 4.5 s (P=4*10$^{-5}$, paired t-test). The labels $C_1\alpha$ and $C_1\beta$ (FIG. 1-3) mark the two signals of the glucose carbon at position 1 in the α and β anomers. The labels $C_i\alpha$ and $C_i\beta$ (FIG. 1-3) mark the two signals of the glucose carbon at position i in the α and β anomers. This investigation showed that the $T_1$ of glucose carbons was affected by the concentration and suggested that the physiological conditions are favorable for $T_1$ elongation. It also suggested that hyperpolarized glucose concentration should be kept at a minimum during the transfer of the hyperpolarized media from the polarizer to the subject and during the administration to the subject.

The effect of the magnetic field strength on the $T_1$ of glucose carbons was investigated at 7 T (FIG. 2, solid gray columns) and at 11.8 T (FIG. 2, diagonal pattern columns). [U-$^{13}C_6$, $^2H_7$]glucose $T_1$ at 400 mM was measured using the inversion recovery pulse sequence in the two spectrometers. The $T_1$ of glucose carbons was found to be longer in the lower magnetic field (7 T). The mean difference in $T_1$ between the two fields was 2 s (P=6*10$^{-4}$, paired t-test). This suggests that the glucose carbons' $T_1$ may be longer at clinically relevant magnetic field strengths (1.5 T and 3 T). Further studies are underway to validate this suggestion.

To increase the signal of hyperpolarized deoxy-glucose and hyperpolarized glucose, stable isotope labeling by carbon-13 in all of the carbon positions was used. The effect of direct carbon-13 to carbon-13 bonding on the individual carbon-13 $T_1$s was investigated to study the effect of these added dipolar interactions on $T_1$ relaxation times. To this end, two compounds were investigated (both from Cambridge Isotopes Laboratories): [U-$^{13}C_6$, $^2H_7$]glucose (FIG. 3, solid gray columns) and [$^2H_7$]glucose (FIG. 3, diagonal pattern columns), both at 400 mM concentration. The $T_1$ at 11.8 T was measured using the inversion recovery pulse sequence. While both compounds are fully deuterated, in the [U-$^{13}C_6$, $^2H_7$]glucose molecule the carbon positions are 99% occupied by $^{13}$C nuclei. In the [$^2H_7$]glucose molecule, only ca. 1.1% of each of the carbon positions are occupied by $^{13}$C nuclei (due to the natural abundance distribution of $^{13}$C). The chance for having two directly bonded $^{13}$C nuclei in this molecule is therefore 0.01% (negligible). Therefore this measurement was indicative of the $T_1$ of singly $^{13}$C labeled glucose. It was found that the $T_1$ of glucose $^{13}$Cs in a uniformly $^{13}$C-labeled glucose was shorter by 3.3 s (P=1.4×10$^{-3}$, paired t-test). Therefore, it was deducted that direct bonding of additional $^{13}$C nuclei led to a decrease in glucose $^{13}$C $T_1$s, due to the additional dipolar interactions. However, as can be seen in the following, this decrease in $T_1$ did not prevent imaging of hyperpolarized [U-$^{13}C_6$, $^2H_7$]glucose.

The fully deuterated and fully $^{13}$C labeled [U-$^{13}C_6$, $^2H_7$] glucose has two competing properties, in terms of its potential hyperpolarized signal. On one hand, it is labeled at six positions, all with similar $T_1$. This property can be utilized to increase the initial hyperpolarized signal sixfold. On the other hand, the $T_1$ s of these carbon-13 nuclei are shorter than any hyperpolarized probe reported to date.

Figure 1A:
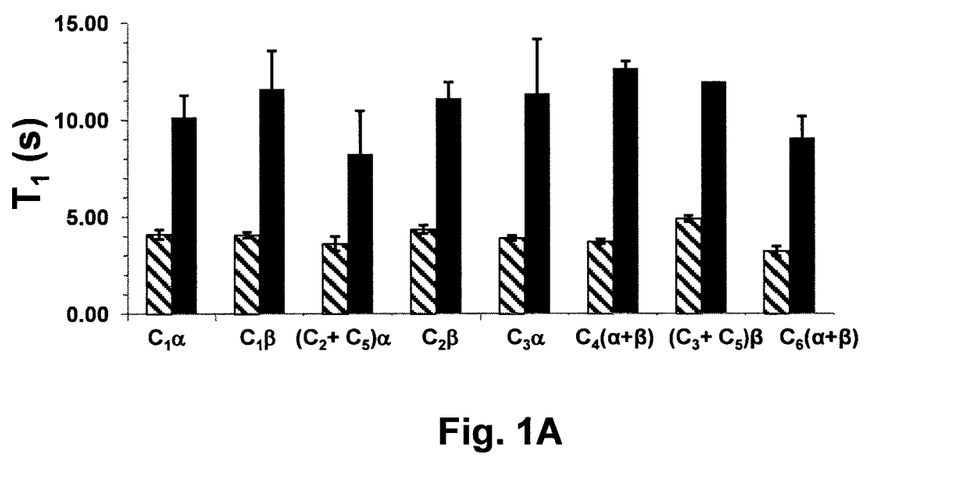
FIGS. 1A-1B show the effect of glucose concentration on the $T_1$ of glucose carbons as measured at 7 T (FIG. 1A) and at 11.8 T (FIG. 1B).
Figure 1B:
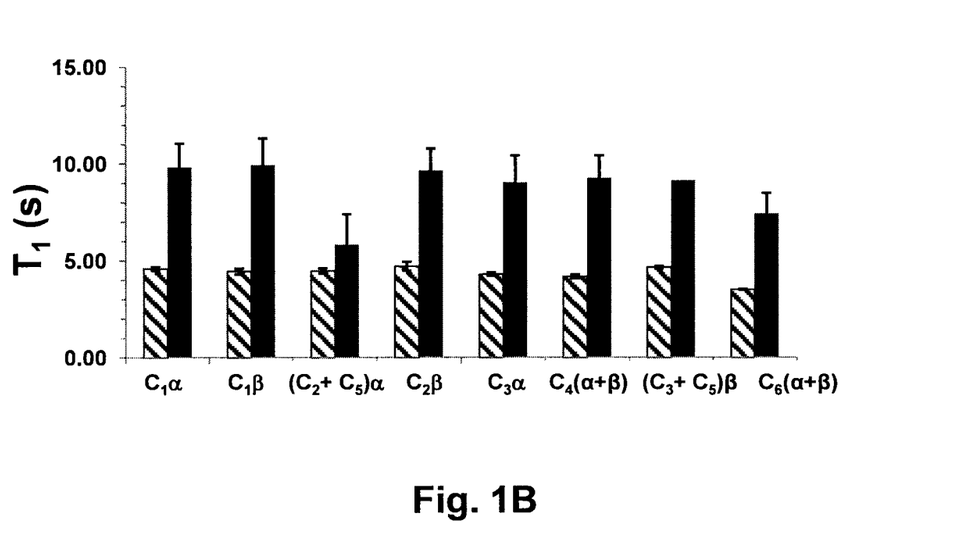
Figure 4:
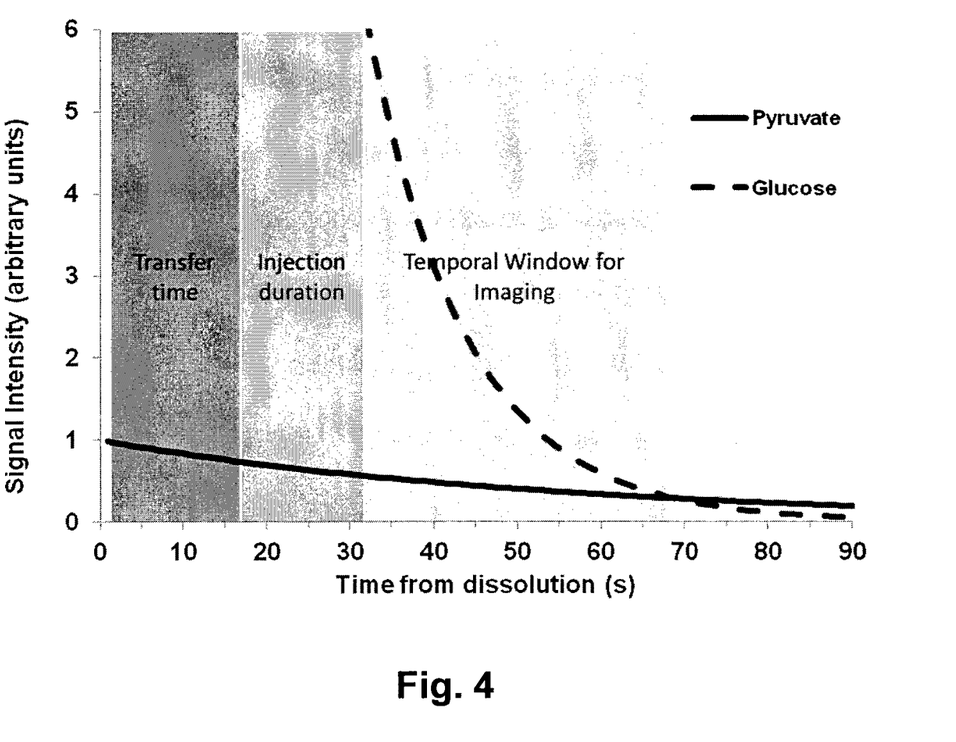
FIG. 4 shows the simulation for the relative imaging signal of [U-$^{13}$C$_6$, $^2$H$_7$]glucose compared to [1-$^{13}$C]pyruvate hyperpolarized molecular probes.

To gain insight into the relative imaging signal increase that would be provided by using glucose or deoxyglucose that are fully labeled with 13C and deuterium in all positions at a hyperpolarized state, a signal enhancement simulation was performed. This simulation compared the signal expected from the deoxy-glucose or glucose molecular probe (FIG. 4, dashed line) to that of the [1-$^{13}$C]pyruvate molecular probe (FIG. 4, solid line). In this calculation the following consideration were taken: 1) pyruvate was injected at a dose of 0.2 mmol/Kg ("Real-Time Metabolic Imaging" *Proc. Natl. Acad. Sci. USA,* 2006, 103, 11270-11275) and glucose was injected at a dose of 1.4 mmol/Kg (which is ca. half of the dose that is safe for injection in humans, as per the glucose tolerance test); 2) the imaging signal is greater than the spectroscopic signal by an estimated factor of approximately 2.5 (in comparison to the pyruvate study described above); 3) the initial relative imaging signal is dependent both on the dose ratio and the imaging signal strength compared to that of spectroscopy; 4) the $T_1$ of pyruvate is 55 s; 5) the $T_1$ of glucose is position and anomer dependent, the individual values were determined per position and were used in this calculation (8-13 s). The glucose signal at each time point was calculated as $\Sigma Sc_i$, where $Sc_i$ is the individual signal for each carbon position at a particular time point. Each $Sc_i$ was calculated according to $Sc_i(t)=I_{SNR}\cdot\exp(-t/T_{1\_ci})$, where $I_{SNR}$ is the initial SNR or the initial relative imaging signal (pyruvate initial signal multiplied by the dose ratio factor and the imaging/spectroscopy signal increase factor as defined above). $T_{1\_ci}$ was individually determined per carbon position (using [U-$^{13}C_6$, $^2H_7$]glucose at 7 T and 400 mM, see FIG. 1). In this example it was assumed that the $T_{1\_ci}$ of [U-$^{13}C_6$, $^2H_8$] deoxy-glucose is similar to that of [U-$^{13}C_6$, $^2H_7$]glucose.

Considering a duration of approximately 30 s from dissolution start for transfer and injection, this simulation suggests a temporal window for imaging of approximately 35 s more, during which the expected signal of hyperpolarized [U-$^{13}C_6$, $^2H_7$]glucose is higher than that of hyperpolarized [1-$^{13}$C]pyruvate (FIG. 4). The simulation also suggests that a dramatic increase in signal may be gained using hyperpolarized [U-$^{13}C_6$, $^2H_7$]glucose by minimizing the transfer and/or the injection duration.

Figure 5A:
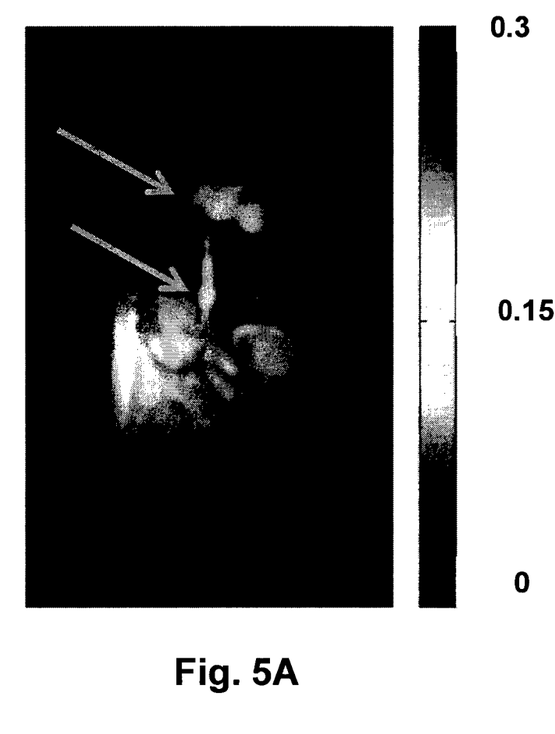
FIGS. 5A-5C show hyperpolarized [U-$^{13}$C$_6$, $^2$H$_7$]glucose in vivo images at 3 T, recorded in rats injected through the tail vein in a bolus of 12 s total duration. Images were recorded at 8 s (FIG. 5A), 12 s (FIG. 5B), and 20 s (FIG. 5C) from the onset of the bolus injection (i.e. during and after the bolus).
Figure 5B:
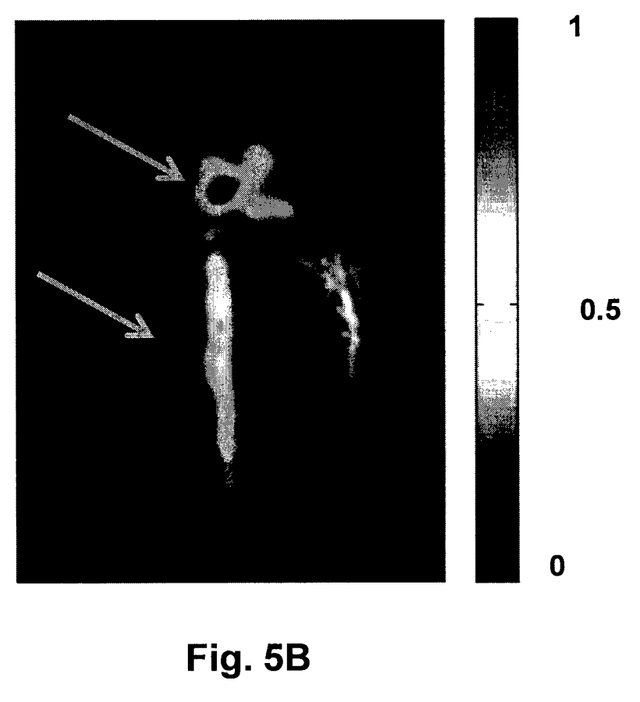
Figure 5C:
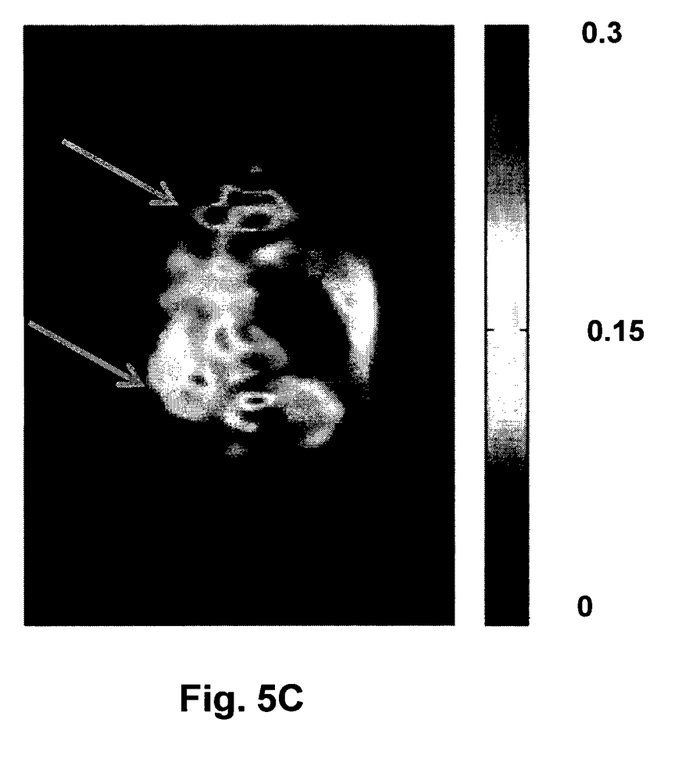

Hyperpolarized glucose images were recorded at 3 T in vivo. As depicted in FIG. 5, hyperpolarized [U-$^{13}C_6$, $^2H_7$] glucose provided a high signal on carbon-13 images recorded in vivo. Normal rats were anesthetized, and hyperpolarized [U-$^{13}C_6$, $^2H_7$]glucose was injected through the tail vein in a bolus of 12 s total duration. Images were recorded at 8, 12, and 20 s from the onset of the bolus injection (i.e. during and after the bolus).

In the image recorded at 8 s (FIG. 5A), the inferior vena cava and the heart are clearly visible (see indicating arrows). Arterial hyperpolarized media flow at this time is not likely, as the signal in the kidneys is not yet visible. This image, which was recorded during the bolus at a very high resolution (128×128 matrix, in-plane resolution of 1.56 mm), demonstrates the use of hyperpolarized glucose imaging in angiography. The signal from the injected hyperpolarized media is extremely high with no background signal.

At 12 s (FIG. 5B), at the end of the bolus injection, signal intensity in the main vasculature and the heart is still high, with substantial intensity observed in the kidneys (see indicating arrows).

At 20 s from bolus initiation (FIG. 5C), signal from the heart is the most intense signal in the image, about 40% higher than signal in the vasculature and 20% higher than signal in the kidneys. Still, signal in the kidneys is clearly observed, as well as signal in other tissues such as the liver (see indicating arrows and color change).

The hyperpolarized glucose signal observed in the heart at 20 s from bolus start is more intense than signal in the vasculature and the kidneys. It is thus suggested that this intense signal in the heart indicates glucose uptake in the myocardium. In the anaesthetized rat, the only tissue that is expected to actively take up glucose is the myocardium, because under anesthesia it is the only active muscle. The brain, which very actively takes up glucose in conscious subjects, as seen on clinical FDG-PET images, actually has very low glucose metabolism under anesthesia, and was therefore not imaged. It is noted that heart anatomy cannot be discerned from these hyperpolarized images since the imaging time (1 s) averaged several heart beats (approximately 6 beats). However, glucose uptake by the myocardium can be determined at short time frames of the order of 20 s using gradient de-phasing of intravoxel moving spins. Using this methodology, hyperpolarized glucose or deoxyglucose signal from capillaries are diminished, while the signal of intracellular hyperpolarized glucose or deoxyglucose are imaged and indicate the level of glucose uptake in the tissue.

The reference in this specification to any prior publication (or information derived from it), or to any matter which is known, is not, and should not be taken as an acknowledgement or admission or any form of suggestion that that prior publication (or information derived from it) or known matter forms part of the common general knowledge in the field of endeavor to which this specification relates.

The invention claimed is:

1. Deoxy-glucose comprising six isotopically labeled carbon atoms each of said isotopically labeled carbon atoms is directly bonded to at least one deuterium atom.

2. Deoxy-glucose according to claim 1, wherein said isotopically labeled carbon atom is $^{13}$C.

3. Deoxy-glucose according to claim 1, having $T_1$ relaxation time values of $^{13}$C nuclei of between about 2 to about 60 sec.

4. Deoxy-glucose according to claim 1, further comprising at least one isotopically labeled hydrogen atom.

5. Deoxy-glucose according to claim 1, further comprising at least one fluorine atom.

6. Deoxy-glucose according to claim 1, being [$^{13}$C$_6$, D$_8$]2-deoxyglucose.

7. Deoxy-glucose according to claim 1, being in a hyperpolarized state.

8. A composition comprising at least one deoxy-glucose comprising six isotopically labeled carbon atoms each of said isotopically labeled carbon atoms is directly bonded to at least one deuterium atom.

9. A kit comprising at least one component containing at least one deoxy-glucose comprising six isotopically labeled carbon atoms each of said isotopically labeled carbon atoms is directly bonded to at least one deuterium atom and instructions for use.

10. A kit according to claim 9, wherein said instructions are for use in diagnosing and evaluating a state, condition, or disease.

* * * * *